United States Patent [19]

Anderson et al.

[11] Patent Number: 4,544,400
[45] Date of Patent: Oct. 1, 1985

[54] COMPOSITIONS

[75] Inventors: Richard J. Anderson, Palo Alto; Michael M. Leippe, Boulder Creek, both of Calif.

[73] Assignee: Zoecon Corporation, Palo Alto, Calif.

[21] Appl. No.: 514,749

[22] Filed: Jul. 18, 1983

Related U.S. Application Data

[62] Division of Ser. No. 351,070, Feb. 22, 1982, abandoned.

[51] Int. Cl.[4] ............... C07D 271/08; C07D 285/10; A01N 43/26
[52] U.S. Cl. .......................................... 71/90; 71/92; 548/126
[58] Field of Search ...................... 548/126; 71/90, 92

[56] References Cited

U.S. PATENT DOCUMENTS 4,185,018  1/1980  Fäh ..................................... 548/126

FOREIGN PATENT DOCUMENTS 660379  8/1965  Belgium .

OTHER PUBLICATIONS

Chem. Abs. vol. 64: 2098b–Abstract of Belg. 660379 (1966).

Primary Examiner—Robert Gerstl
Attorney, Agent, or Firm—Hana Dolezalova; Jacqueline Larson

[57] ABSTRACT

Substituted phenoxy- and pyridyloxybenzo-2,1,3-oxadiazoles, phenoxy- and pyridyloxybenzo-2,1,3-thiadiazoles, and the N-oxides thereof, intermediates therefor, synthesis thereof, and the use of said compounds for the control of weeds.

16 Claims, No Drawings

COMPOSITIONS

This is a division of application Ser. No. 351,070, filed Feb. 22, 1982, now abandoned.

This invention relates to substituted phenoxy- and pyridyloxybenzo-2,1,3-oxadiazoles, phenoxy- and pyridyloxybenzo-2,1,3-thiadiazoles, and the N-oxides thereof, intermediates therefor, synthesis thereof, and the use of said compounds for the control of weeds.

The compounds of the present invention are represented by the following formula (A):

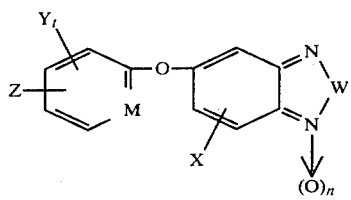

wherein,
M is CH or N;
n is zero or one;
t is zero, one or two;
W is oxygen or sulfur; and
each of the X, Y and Z is independently selected from hydrogen, lower alkyl, lower haloalkyl, lower alkoxy, lower alkylthio, lower alkoxycarbonyl, acyl, halogen, cyano, nitro or amino.

Hereinafter, each of M, n, t, W, X, Y and Z is as defined above, unless otherwise specified.

The compounds of formula A where W is oxygen can be prepared as outlined below:

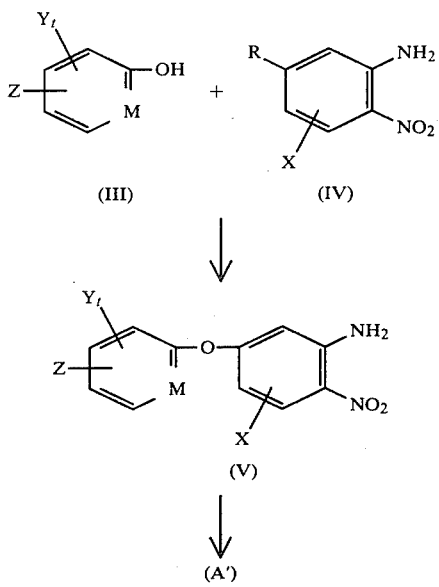

In the above synthesis, a phenol or pyridyl alcohol (III) is reacted with a halonitroaniline (IV) in the presence of potassium carbonate and in a solvent such as dimethylsulfoxide (DMSO) or tetrahydrofuran (THF) at room temperature or above to give the corresponding phenoxy- or pyridyloxynitroaniline (V). This is reacted with sodium hypochlorite at room temperature to give the benzoxadiazole N-oxide (A').

The compounds of formula (V) can alternately be prepared by reacting a phenol or pyridyl alcohol of

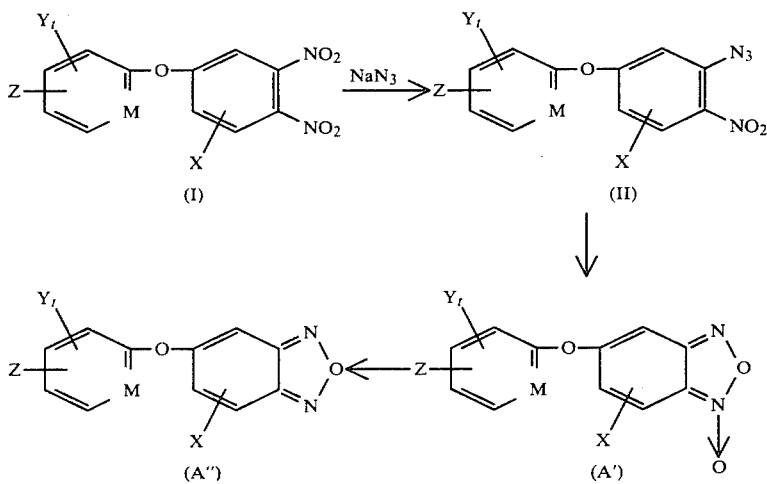

In the above synthesis, a dinitrobenzene (I) is reacted with sodium azide at reflux temperature and in solvent such as acetone to give the corresponding nitrophenyl azide (II). The azide (II) is heated under reflux to give the benzooxadiazole N-oxide (A'), which can then be reduced by reaction with a reducing agent such as triethyl phosphite, PCl$_5$, triphenylphosphine or hydroxylamine alkali to give the benzoxadiazole (A'').

Alternately, the compounds of formula A' can be synthesized as follows (R is halo):

formula (III) with an N-substituted halonitroaniline (IV') and potassium carbonate in a solvent such as DMSO or THF at room temperature or above. The resulting N-substituted phenoxy- or pyridyloxynitroaniline (V') is reacted with a strong acid such as hydrochloric acid at elevated temperature to give the nitroaniline of formula (V) (R' is lower alkyl).

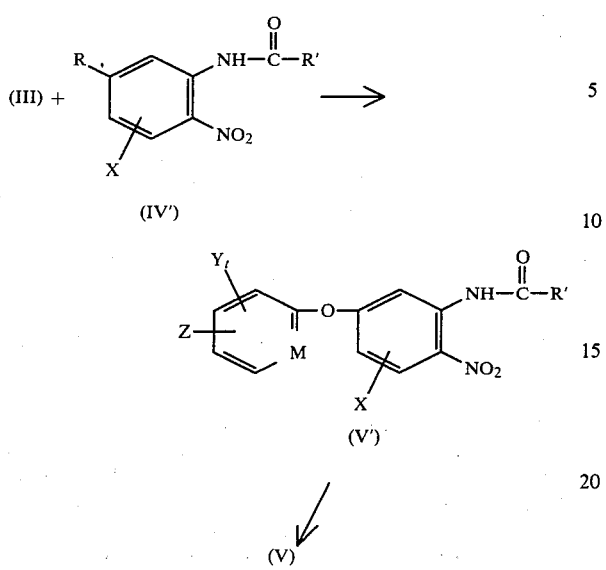

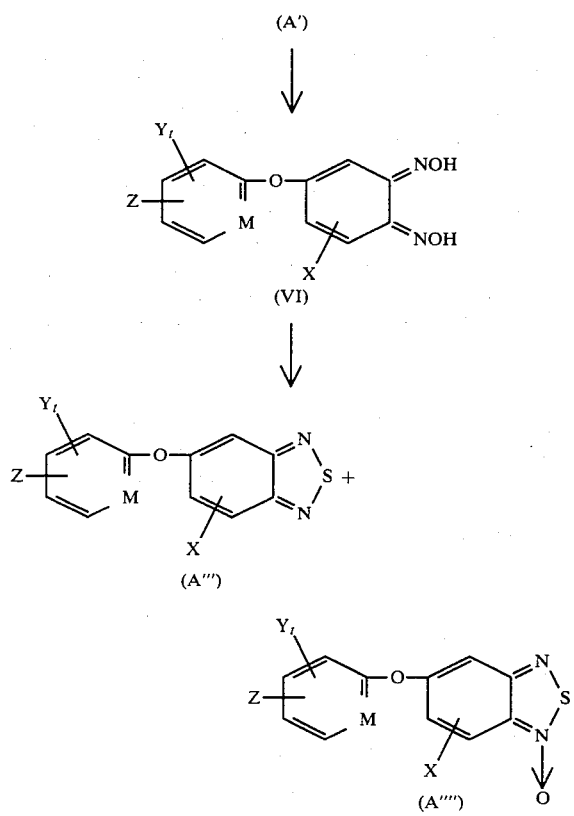

To prepare compounds of formula A where W is sulfur, a N-oxide of formula A' is reduced by reaction with a reducing agent such as hydroxylamine to give the corresponding dioxime (VI). The dioxime (VI) is reacted with a source of sulfur atoms such as thionyl chloride, sulfur dichloride or N-thionyl aniline to yield a mixture of benzothiadiazole (A''') and benzothiadiazole N-oxide (A'''').

Compounds of formula A''' may also be synthesized as follows:

A dinitrobenzene (I) is reacted with, for example, ammonium chloride and iron or with hydrogen gas and palladium on activated carbon in a solvent such as ethanol or toluene and at elevated temperature to give the corresponding aminoaniline (VII). The aminoaniline (VII) is reacted with, for example, thionyl chloride, N-thionyl aniline or sulfur dichloride in a solvent such as toluene or ethanol and at elevated temperature to yield a benzothiadiazole of formula (A''').

The following terms, wherever used in the description herein and in the appended claims, have the meaning defined below, unless otherwise specified hereinafter.

The term "lower alkyl" refers to an alkyl group, straight or branched, of one to six carbon atoms.

The term "lower haloalkyl" refers to a haloalkyl group, straight or branched, of one to six carbon atoms substituted with at least one halo atom.

The term "lower alkoxy" refers to an alkoxy group, straight or branched, of one to six carbon atoms.

The term "lower alkylthio" refers to an alkylthio group, straight or branched, of one to six carbon atoms.

The term "lower alkoxycarbonyl" refers to an alkoxycarbonyl group, straight or branched, of two to six carbon atoms.

The term "acyl" refers to an acyl group, straight or branched, of two to six carbon atoms.

The novel compounds of formula A are useful for the control of weeds, using pre- and/or post-emergent treatment. The compounds can be applied in the form of dusts, granules, solutions, emulsions, wettable powders, flowables and suspensions. Application of a compound of the present invention is made according to conventional procedure to the weeds or their locus using an herbicidally effective amount of the compound, usually from about one-half or less to ten pounds per acre.

Methods of preparing herbicidal formulations which can be used with a compound of the present invention are described in the literature along with suitable liquid and solid carriers, such as in U.S. Pat. Nos. 4,192,669 and 4,163,661, which are incorporated herein by reference. The compounds of the present invention have herbicidal activity on both broadleaf plants and the grassy or graminaceous weeds. The optimum usage of a compound of the present invention is readily determinable by one of ordinary skill in the art using routine testing such as greenhouse testing and small plot testing.

The term "herbicide," as used herein, refers to an active ingredient which modifies the growth of plants because of phytotoxic or plant growth regulating properties so as to retard the growth of the plant or damage the plant sufficiently to kill it.

The compounds of the present invention can exist in tautomeric form, one of which is represnted by formula A and the other, by formula B. Both forms are embraced by this invention.

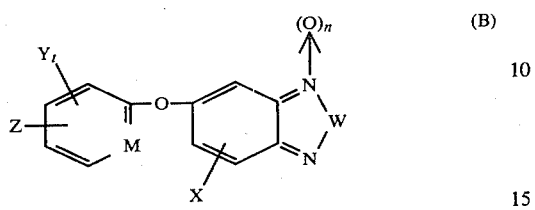

The following examples are provided to illustrate the practice of the present invention. Temperature is given in degrees centigrade. "RT" means room temperature.

EXAMPLE 1

A mixture of 4-(2-chloro-4-trifluoromethylphenoxy)-1,2-dinitrobenzene (2.0 g, 5.5 mmol) and sodium azide (1.1 g, 16.6 mmol) in acetone (25 ml) is heated under reflux for 3.5 hours. The reaction is then cooled and filtered, and the filtrate is stripped. The residue is taken up in chloroform, washed with water (2X) and with brine, dried, stripped and purified by preparative thin layer chromatography (prep. TLC) (silica gel, eluting with 15% ethyl acetate/hexane) to give 5-(2-chloro-4-trifluoromethylphenoxy)-2-nitrophenyl azide.

5-(2-Chloro-4-trifluoromethylphenoxy)-2-nitrophenyl azide (1.2 g) is cautiously heated to reflux temperature in toluene (10 ml) and is heated under reflux for 3 hours. The reaction is cooled, and diluted with benzene, washed with water (3X) and with brine, dried, stripped and purified by prep. TLC (6.5% ethyl acetate/hexane) to give 5-(2-chloro-4-trifluoromethylphenoxy)-benzo-2,1,3-oxadiazole N-oxide, m.p. 60°–61°. (C; X=H, Y=Cl, Y'=H, Z=CF₃).

EXAMPLE 2

A mixture of 5-(2-chloro-4-trifluoromethylphenoxy)-benzo-2,1,3-oxadiazole N-oxide (2.0 g) and triethyl phosphite (10 ml) is heated under reflux in ~150 ml of ethanol for 4 hours. The reaction is cooled and stripped, and the crude product is purified by prep. TLC (15% ethyl acetate/hexane) to give 5-(2-chloro-4-trifluoromethylphenoxy)benzo-2,1,3-oxadiazole, m.p. 65°–66°.

EXAMPLE 3

A mixture of 4-(2-chloro-4-trifluoromethylphenoxy)-1,2-dinitrobenzene (2.1 g, 5.8 mmol) and ammonium chloride (6.2 g, 116.0 mmol) is heated in ethanol/water (40 ml/20 ml) to 70°. Iron powder (3.2 g, 58.0 mmol) is added in small portions over 15 minutes, and the mixture is then heated under reflux ... ours. The reaction is filtered through celite and stripped. The residue is taken up in ether, washed with water, dried and stripped to give 4-(2-chloro-4-trifluoromethylphenoxy)-2-aminoaniline.

4-(2-Chloro-4-trifluromethylphenoxy)-2-aminoaniline (1.4 g, 4.6 mmol) in ~15 ml of toluene is added quickly to a stirring solution of thionyl chloride (1.7 g, 13.0 mmol) in 70 ml of toluene. The reaction is heated under reflux for 24 hours, then is cooled to RT and is stripped. The residue is washed several times with hexane, and the combined hexane washes are stripped and purified by prep TLC to give 5-(2-chloro-4-trifluoromethylphenoxy)-benzo-2,1,3-thiadiazole, a dark red liquid.

IR (smear) 1610, 1580, 1323, 1265 and 1082 cm⁻.

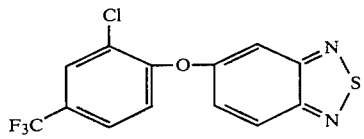

EXAMPLE 4

N-methylcarbonyl 3-fluoroaniline (5 g, 32.0 mmol) is dissolved in 25 ml of conc. sulfuric acid and is cooled to 0°. A mixture of 90% nitric acid (2.5 ml) in conc. sulfuric acid (25 ml) is added dropwise over a period of about 1 hour, with the temperature maintained at 0°. The reaction is allowed to warm to RT and is stirred at RT for 3 hours. The reaction is then carefully poured into ice. The resulting solid is washed several times with 10% ethyl acetate/hexane, and the combined organic extracts are stripped to give N-methylcarbonyl 2-nitro-5-fluoroaniline.

A mixture of 2,4-dichlorophenol (1.2 g, 7.6 mmol) and potassium carbonate (2.1 g, 15.2 mmol) is stirred together in dimethylsulfoxide (20 ml). N-methylcarbonyl 2-nitro-5-fluoroaniline (1.5 g, 7.6 mmol) is added in portions. After 1 hour, the reaction is heated to 100° for 1.5 hours. The reaction is then cooled to RT and diluted with water. A solid is collected, dissolved in chloroform, washed with water, dried and stripped to give N-methylcarbonyl 2-nitro-5-(2,4-dichlorophenoxy)aniline.

N-methylcarbonyl 2-nitro-5-(2,4-dichlorophenoxy)aniline (2.0 g, 5.9 mmol) in 50 ml of 10% hydrochloric acid is heated under reflux for 2 hours. The reaction is cooled to RT, 10 ml of ethanol is added, and the reaction is heated under reflux for another 4 hours. The reaction is cooled to RT, made slightly basic with 20% sodium hydroxide and extracted with ether. The combined extracts are washed with water, dried and stripped to give 2-nitro-5-(2,4-dichlorophenoxy)aniline.

2-Nitro-5-(2,4-dichlorophenoxy)aniline (1.6 g, 5.4 mmol) is dissolved in a solution of potassium hydroxide (0.33 g, 5.9 mmol) in ~150 ml of ethanol. The mixture is cooled to −5°, and sodium hypochlorite (17 ml of 5.3% solution, 0.9 g, 11.8 mmol) is added dropwise over 20 minutes. The reaction is stirred at RT overnight, then cooled to 10° and ~2 ml of sodium hypochlorite is added. One hour later, the reaction is stripped. The residue is taken up in ether, washed with water, dried, stripped and purified by prep. TLC (10% ethyl acetate/hexane) to yield 5-(2,4-dichlorophenoxy)benzo-2,1,3-oxadiazole N-oxide, m.p. 92°–93°.

Following the procedure of Example 2, 5-(2,4-dichlorophenoxy)benzo-2,1,3-oxadiazole N-oxide is reduced to yield 5-(2,4-dichlorophenoxy)benzo-2,1,3-oxadiazole.

EXAMPLE 5

Following the procedure of Example 4, N-methylcarbonyl 2-nitro-5-fluoroaniline (1.0 g, 5.1 mmol), phenol (0.47 g, 5.1 mmol) and potassium carbonate (1.4 g, 10.2 mmol) are reacted together to give N-methylcarbonyl 2-nitro-5-phenoxyaniline, 1.2 g of which is then reacted with 20% hydrochloric acid (50 ml) to give 2-nitro-5- phenoxyaniline. The 2-nitro-5-phenoxyaniline (0.9 g, 3.9 mmol) is reacted with potassium hydroxide (0.2 g, 3.9 mmol) and sodium hypochlorite (11 ml of 5.2% solution, 0.6 g, 7.8 mmol) to yield 5-phenoxybenzo-2,1,3-oxadiazole N-oxide, m.p. 76°–77°.

Following the procedure of Example 2, 5-phenoxybenzo-2,1,3-oxadiazole N-oxide is reduced to give 5-phenoxybenzo-2,1,3-oxadiazole.

EXAMPLE 6

Following the procedure of Example 4, N-methylcarbonyl 2-nitro-5-fluoroaniline (3.1 g, 15.4 mmol), 4-trifluoromethylphenol (2.5 g, 15.4 mmol) and potassium carbonate (4.3 g, 31.0 mmol) are reacted together to give N-methylcarbonyl 2-nitro-5-(4-trifluoromethylphenoxy)aniline, 4.0 g of which is then reacted with 20% hydrochloric acid (~50 ml) to give 2-nitro-5-(4-trifluoromethylphenoxy)aniline. 2-Nitro-5-(4-trifluoromethylphenoxy)aniline (2.0 g, 6.7 mmol) is reacted with potassium hydroxide (0.4 g, 7.0 mmol) and sodium hypochlorite (19 ml of 5.2% solution, 1.0 g, 13.4 mmol) to yield 5-(4-trifluormethylphenoxy)benzo-2,1,3-oxadiazole N-oxide, m.p. 40°–42°.

Following the procedure of Example 2, 5-(4-trifluoromethylphenoxy)benzo-2,1,3-oxadiazole N-oxide (0.7 g) and triethyl phosphite (5 ml) in 75 ml of ethanol are heated under reflux for 2 hours. The reaction is cooled and stripped, and the residue is purified to give 5-(4-trifluoromethylphenoxy)benzo-2,1,3-oxadiazole, m.p. 77°–78°.

EXAMPLE 7

Following the procedure of Example 4, each of the anilines under col. I is reacted with potassium hydroxide and sodium hypochlorite to give the corresponding benzoxadiazole N-oxide under col. II, each of which is then reduced following the procedure of Example 2 to give the corresponding benzoxadiazole under col. III.

I 1. 2-nitro-5-(4-methylphenoxy)aniline
2. 2-nitro-5-(4-ethoxyphenoxy)aniline
3. 2-nitro-5-(4-chloro-2-nitrophenoxy)aniline
4. 2-nitro-5-(4-chloro-2-cyanophenoxy)aniline
5. 2-nitro-5-(2,6-dichloro-4-trifluoromethylphenoxy)aniline
6. 2-nitro-5-(4-methylcarbonylphenoxy)aniline
7. 2-nitro-5-(4-methoxycarbonylphenoxy)aniline
8. 2-nitro-5-(4-bromophenoxy)aniline
9. 2-nitro-5-(2-fluoro-4-trifluoromethylphenoxy)aniline
10. 2-nitro-5-(2-bromo-4-chlorophenoxy)aniline

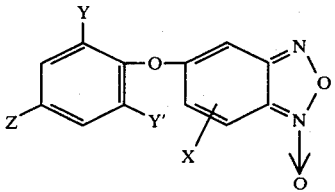

(C)

| | X | Y | Y' | Z |
|---|---|---|---|---|
| 1. | H | H | H | CH₃ |
| 2. | H | H | H | OCH₂CH₃ |
| 3. | H | NO₂ | H | Cl |
| 4. | H | CN | H | Cl |
| 5. | H | Cl | Cl | CF₃ |

-continued

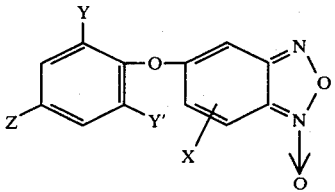

(C)

| | X | Y | Y' | Z |
|---|---|---|---|---|
| 6. | H | H | H | C(O)CH₃ |
| 7. | H | H | H | C(O)OCH₃ |
| 8. | H | H | H | Br |
| 9. | H | F | H | CF₃ |
| 10. | H | Br | H | Cl |

III 1. 5-(4-methylphenoxy)benzo-2,1,3-oxadiazole
2. 5-(4-ethoxyphenoxy)benzo-2,1,3-oxadiazole
3. 5-(4-chloro-2-nitrophenoxy)benzo-2,1,3-oxadiazole
4. 5-(4-chloro-2-cyanophenoxy)benzo-2,1,3-oxadiazole
5. 5-(2,6-dichloro-4-trifluoromethylphenoxy)benzo-2,1,3-oxadiazole
6. 5-(4-methylcarbonylphenoxy)benzo-2,1,3-oxadiazole
7. 5-(4-methoxycarbonylphenoxy)benzo-2,1,3-oxadiazole
8. 5-(4-bromophenoxy)benzo-2,1,3-oxadizaole
9. 5-(2-fluoro-4-trifluoromethylphenoxy)benzo-2,1,3-oxadiazole
10. 5-(2-bromo-4-chlorophenoxy)benzo-2,1,3-oxadiazole The anilines under col. I are prepared by reacting N-methylcarbonyl 2-nitro-5-fluoroaniline with each of the corresponding phenols, followed by reaction with 20% HCl, following the procedure of Example 4.

EXAMPLE 8

To iodobenzene diacetate (3.9 g, 12 mmol) in 100 ml of acetone is added at RT 2-nitro-5-(3,5-dichloro-2-pyridyloxy)aniline (3.0 g, 10 mmol), neat, in portions over 10 minutes. The reaction is stirred at RT overnight and is then stripped. Chloroform is added to the residue, and this mixture is filtered through celite. The filtrate is washed with water (2X) and with brine, dried over sodium sulfate and stripped to give 5-(3,5-dichloro-2-pyridyloxy)benzo-2,1,3-oxadiazole N-oxide. (D; X=H, Y=Cl, Z=Cl).

In the same way, each of the anilines under col. IV is reacted with iodobenzene diacetate to give the corresponding benzoxadiazole N-oxide under col. V.

IV 11. 2-nitro-5-(3-chloro-5-trifluoromethyl-2-pyridyloxy)aniline
12. 2-nitro-5-(2-pyridyloxy)aniline
13. 2-nitro-5-(5-trifluoromethyl-2-pyridyloxy)aniline
14. 2-nitro-5-(5-methyl-2-pyridyloxy)aniline
15. 2-nitro-5-(5-ethoxy-2-pyridyloxy)aniline
16. 2-nitro-5-(5-chloro-3-nitro-2-pyridyloxy)aniline
17. 2-nitro-5-(5-methylcarbonyl-2-pyridyloxy)aniline
18. 2-nitro-5-(3-fluoro-5-trifluoromethyl-2-pyridyloxy)aniline
19. 2-nitro-5-(3-bromo-5-chloro-2-pyridyloxy)aniline
20. 2-nitro-5-(5-chloro-3-cyano-2-pyridyloxy)aniline

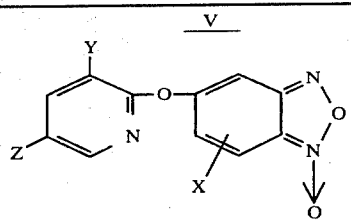

V (D)

| | X | Y | Z |
|---|---|---|---|
| 11. | H | Cl | $CF_3$ |
| 12. | H | H | H |
| 13. | H | H | $CF_3$ |
| 14. | H | H | $CH_3$ |
| 15. | H | H | $OCH_2CH_3$ |
| 16. | H | $NO_2$ | Cl |
| 17. | H | H | $C(O)CH_3$ |
| 18. | H | F | $CF_3$ |
| 19. | H | Br | Cl |
| 20. | H | CN | Cl |

Following the procedure of Example 2, 5-(3,5-dichloro-2-pyridyloxy)benzo-2,1,3-oxadiazole N-oxide is reduced to give 5-(3,5-dichloro-2-pyridyloxy)benzo-2,1,3-oxadiazole. In the same way, each of the N-oxides under col. V is reduced to give the corresponding benzoaxadiazole under col. VI.

VI 11. 5-(3-chloro-5-trifluoromethyl-2-pyridyloxy)benzo-2,1,3-oxadiazole
12. 5-(2-pyridyloxy)benzo-2,1,3-oxadiazole
13. 5-(5-trifluoromethyl-2-pyridyloxy)benzo-2,1,3-oxadiazole
14. 5-(5-methyl-2-pyridyloxy)benzo-2,1,3-oxadiazole
15. 5-(5-ethoxy-2-pyridyloxy)benzo-2,1,3-oxadiazole
16. 5-(5-chloro-3-nitro-2-pyridyloxy)benzo-2,1,3-oxadiazole
17. 5-(5-methylcarbonyl-2-pyridyloxy)benzo-2,1,3-oxadiazole
18. 5-(3-fluoro-5-trifluoromethyl-2-pyridyloxy)benzo-2,1,3-oxadiazole
19. 5-(3-bromo-5-chloro-2-pyridyloxy)benzo-2,1,3-oxadiazole
20. 5-(5-chloro-3-cyano-2-pyridyloxy)benzo-2,1,3-oxadiazole 2-Nitro-5-(3,5-dichloro-2-pyridyloxy)aniline and the anilines under col. IV are prepared by reacting N-methylcarbonyl 2nitro-5-fluoroaniline with each of the corresponding 2-pyridyl alcohols, followed by reaction with 20% HCl, following the procedure of Example 4.

EXAMPLE 9

Following the procedure of Example 3, each of 4-(2,4-dichlorophenoxy)-1,2-dinitrobenzene, 4-(2-fluoro-4-trifluoromethylphenoxy)-1,2-dinitrobenzene, 4-(3-chloro-5-trifluoromethyl-2-pyridyloxy)-1,2-dinitrobenzene and 4-(3,5-dichloro-2-pyridyloxy)-1,2-dinitrobenzene is reacted with ammonium chloride in the presence of iron to give, respectively, 4-(2,4-dichlorophenoxy)-2-aminoaniline,
4-(2-fluoro-4-trifluoromethylphenoxy)-2-aminoaniline,
4-(3-chloro-5-trifluoromethyl-2-pyridyloxy)-2-aminoaniline, and
4-(3,5-dichloro-2-pyridyloxy)-2-aminoaniline.

Each of the above aminoanilines is reacted with thionyl chloride to yield, respectively, 5-(2,4-dichlorophenoxy)benzo-2,1,3-thiadiazole,
5-(2-fluoro-4-trifluoromethylphenoxy)benzo-2,1,3-thiadiazole,
5-(3-chloro-5-trifluoromethyl-2-pyridyloxy)benzo-2,1,3-thiadiazole, and
5-(3,5-dichloro-2-pyridyloxy)benzo-2,1,3-thiadiazole.

EXAMPLE 10

Post-emergence herbicidal activity on the grasses (GR) green foxtail, watergrass, shattercane and wild oats and on the broadleafs (BL) annual morningglory, mustard, soybean and velvetleaf was tested for the compounds of Examples 1 and 2 (test compounds No. 1 and 2) by spraying seedlings with a solution of water/acetone (1:1), surfactant (1%) and the test compound at a rate equivalent to 10 lb/acre. Scoring was made two weeks after spraying. The average herbicidal activity, in percent control, is given below.

Pre-emergent herbicidal activity of test compounds No. 1 and 2 was tested on the above-listed grasses and broadleafs (but with nightshade substituted for soybean) at a rate equivalent to 10 lb/acre. The average herbicidal activity, in percent control, is given below.

| Compound No. | Post | | Pre | |
|---|---|---|---|---|
| | GR | BL | GR | BL |
| 1 | 99 | 95 | 93 | 93 |
| 2 | 100 | 79 | 90 | 99 |

EXAMPLE 11

5-(2-Chloro-4-trifluoromethylphenoxy)benzo-2,1,3-oxadiazole N-oxide (1.5 g, 4.5 mmol) is dissolved in 25 ml of ice-cold conc. sulfuric acid. To this is added dropwise 0.32 g (5.0 mmol) of nitric acid dissolved in 5 ml of conc. sulfuric acid. The mixture is allowed to stand for 30 minutes at 0°, and is then poured onto 100 g of ice. The solid is collected to give 4-nitro-5-(2-chloro-4-trifluoromethylphenoxy)benzo-2,1,3-oxadiazole N-oxide.

In the same way, each of 5-(2-chloro-4-trifluoromethylphenoxy)benzo-2,1,3-oxadiazole, 5-(3-chloro-5-trifluoromethyl-2-pyridyloxy)benzo-2,1,3-oxadiazole N-oxide, and 5-(2-chloro-4-trifluoromethylphenoxy)benzo-2,1,3-thiadiazole is nitrated to give, respectively, 4-nitro-5-(2-chloro-4-trifluoromethyl-phenoxy)benzo-2,1,3-oxadiazole,
4-nitro-5-(3-chloro-5-trifluoromethyl-2-pyridyloxy)-benzo-2,1,3-oxadiazole N-oxide, and
4-nitro-5-(2-chloro-4-trifluoromethylphenoxy)benzo-2,1,3-thiadiazole.

EXAMPLE 12

A mixture of 5-(2-chloro-4-trifluoromethylphenoxy)-benzo-2,1,3-oxadiazole N-oxide (20.0 g, 61.0 mmol) and hydroxylamine (4.0 g, 120.00 mmol) in 50 ml of methanol is stirred at 45° for 18 hours. The reaction is cooled to RT and 10 ml of water is added. The resulting white solid which precipitates is collected and dried to give 4-(2-chloro-4-trifluoromethylphenoxy)-ortho-benzoquinone dioxime.

A solution of 5 ml of sulfur dichloride in 25 ml of benzene is added dropwise at 25° to a suspension of 4-(2-chloro-4-trifluoromethylphenoxy)-ortho-benzoquinone dioxime (12.0 g, 36.2 mmol) in 150 ml of benzene. After 2 hours, the reaction is filtered and the filtrate is stripped. The residue is chromatographed on a silica gel column, eluting with 15% ethyl acetate/hexane. The least polar component and the second least polar component are collected to yield, respectively, 5-(2-chloro-4-trifluoromethylphenoxy)benzo-2,1,3-thiadiazole and 5-(2-chloro-4-trifluoromethylphenoxy)benzo-2,1,3-thiadiazole N-oxide.

In the same way, 5-(2,4-dichlorophenoxy)benzo-2,1,3-oxadiazole N-oxide is reduced to the corresponding dioxime, which is then reacted with sulfur dichloride to yield 5-(2,4-dichlorophenoxy)benzo-2,1,3-thiadiazole and 5-(2,4-dichlorophenoxy)benzo-2,1,3-thiadiazole N-oxide.

Likewise, 5-(3-chloro-5-trifluoromethyl-2-pyridyloxy)benzo-2,1,3-oxadiazole N-oxide is reduced, and the resulting dioxime is reacted with sulfur dichloride to give 5-(3-chloro-5-trifluoromethyl-2-pyridyloxy)benzo-2,1,3-thiadiazole and 5-(3-chloro-5-trifluoromethyl-2-pyridyloxy)benzo-2,1,3-thiadiazole N-oxide.

EXAMPLE 13

Nitric acid (30 ml) is cooled to $-5°$, and N-methylcarbonyl 2,3-dichloroaniline (9.8 g, 48 mmol) is added to the acid in small portions, with the temperature maintained at $-5°$ or lower. After the addition is complete, the reaction is stirred for 1 hour at $+5°$. The reaction is then added dropwise to about 150 g of ice-water mixture. The resulting solid is collected by filtration and purified by prep. TLC (developing with 30% ethyl acetate/hexane). The least polar component is isolated to give N-methylcarbonyl 2,3-dichloro-6-nitroaniline.

A mixture of N-methylcarbonyl 2,3-dichloro-6-nitroaniline (0.90 g, 3.6 mmol), 2,4-dichloro-phenol (0.59 g, 3.6 mmol) and potassium carbonate (1.0 g, 7.2 mmol), in 20 ml of DMSO, is stirred at 90° for 3 hours. The reaction is then cooled and poured onto about 60 g of ice. A yellow solid is collected by filtration to give N-methylcarbonyl 2-chloro-3-(2,4-dichloro-phenoxy)-6-nitroaniline.

Following the procedure of Example 4, N-methylcarbonyl 2-chloro-3-(2,4-dichlorophenoxy)-6-nitroaniline is converted, by reaction with HCl, to 2-chloro-3-(2,4-dichlorophenoxy)-6-nitroaniline, which is then reacted with potassium hydroxide and sodium hypochlorite, again following Example 4 procedures, to yield the final product, 4-chloro-5-(2,4-dichlorophenoxy)benzo-2,1,3-oxadiazole N-oxide.

Following the procedure of Example 2, 4-chloro-5-(2,4-dichlorophenoxy)benzo-2,1,3-oxadiazole N-oxide is reduced to yield 4-chloro-5-(2,4-dichlorophenoxy)-benzo-2,1,3-oxadiazole.

What is claimed is:

1. A compound of the formula:

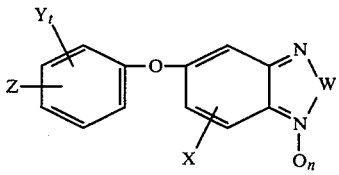
(A)

wherein,
n is zero or one;
t is one or two;
W is sulfur;
X is hydrogen, halogen or nitro; and
each of Y and Z is independently selected from lower alkyl, lower haloalkyl, lower alkoxy, lower alkylthio, lower alkoxycarbonyl, halogen, cyano, nitro or amino.

2. A compound according to claim 1 of the formula:

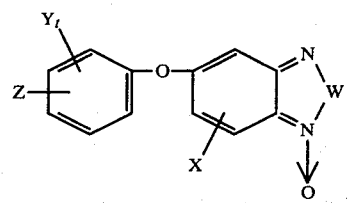

3. A compound according to claim 2 wherein t is one; X is hydrogen, chloro, or nitro; Y is chloro or fluoro; and Z is chloro or trifluoromethyl.

4. A compound of the formula:

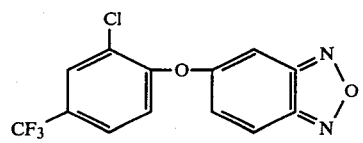

namely, 5(2-chloro-4-trifluoromethylphenoxy)benzo-2,1,3-oxadiazole N-oxide.

5. A compound of the formula:

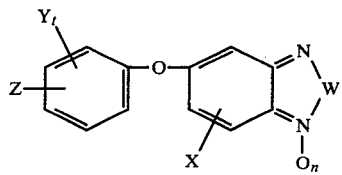

wherein,
n is zero or one;
t is one;
W is sulfur;
X is hydrogen, chloro or nitro;
Y is chloro or fluoro; and
Z is chloro or trifluoromethyl.

6. The compound according to claim 5 wherein X is hydrogen, Y is chloro in the ortho position and Z is chloro or trifluoromethyl in the para position.

7. A compound of the formula:

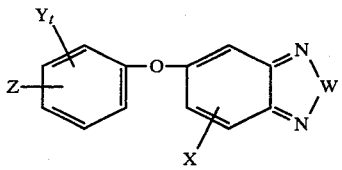

wherein,
t is zero, one or two;
W is oxygen or sulfur;
X is hydrogen, halogen or nitro, and
each of Y and Z is independently selected from lower alkyl, lower haloalkyl, lower alkoxy, lower alkylthio, lower alkoxycarbonyl, halogen, cyano, nitro or amino.

8. A compound according to claim 7 wherein W is oxygen; t is one; X is hydrogen, chloro or nitro; Y is chloro or fluoro; and Z is chloro or trifluoromethyl.

9. The compound according to claim 8 wherein X is hydrogen, Y is chloro in the ortho position and Z is chloro or trifluoromethyl in the para position.

10. The compound 5-(2-chloro-4-trifluoromethylphenoxy)benzo-2,1,3-oxadiazole, according to claim 9.

11. The compound 5-(2,4-dichlorophenoxy)benzo-2,1,3-oxadiazole, according to claim 9.

12. A compound according to claim 7 wherein W is sulfur; t is one; X is hydrogen, chloro or nitro; Y is chloro or fluoro; and Z is chloro or trifluoromethyl.

13. The compound according to claim 12 wherein X is hydrogen, Y is hydrogen or chloro in the ortho position and Z is chloro or trifluoromethyl in the para position.

14. The compound 5-(2-chloro-4-trifluoromethylphenoxy)benzo-2,1,3-thiadiazole, according to claim 13.

15. A method for the control of weeds which comprises treating said weed or its locus with an herbicidally effective amount of a compound of formula (A) as defined in claim 1.

16. A method for the control of weeds which method comprises treating said weed or its locus with an herbicidally effective amount of a compound of claim 4.

* * * * *